United States Patent
Mellin et al.

(10) Patent No.: US 8,858,213 B2
(45) Date of Patent: Oct. 14, 2014

(54) EQUIPMENT AND PROCESSES FOR THE APPLICATION OF ATOMIZED FLUID TO A WEB SUBSTRATE

(71) Applicant: The Procter & Gamble Company, Cincinnati, OH (US)

(72) Inventors: André Mellin, Amberley Village, OH (US); Kevin Benson McNeil, Loveland, OH (US); Peter David Meyer, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 51 days.

(21) Appl. No.: 13/774,172

(22) Filed: Feb. 22, 2013

(65) Prior Publication Data

US 2014/0242210 A1  Aug. 28, 2014

(51) Int. Cl.
| | | |
|---|---|---|
| *D21F 7/00* | (2006.01) | |
| *D21F 3/10* | (2006.01) | |
| *D21G 7/00* | (2006.01) | |
| *D21F 3/08* | (2006.01) | |
| *D21G 1/00* | (2006.01) | |
| *D06B 5/08* | (2006.01) | |

(52) U.S. Cl.
CPC .. *D06B 5/08* (2013.01); *D21F 3/10* (2013.01); *D21G 7/00* (2013.01); *D21F 3/08* (2013.01); *D21G 1/0093* (2013.01); *D21F 7/008* (2013.01)
USPC ........... 425/517; 425/505; 425/508; 425/506; 425/504; 425/363; 425/194; 264/284; 264/299; 34/453; 34/507; 162/204; 162/207; 162/362; 162/368; 162/372

(58) Field of Classification Search
CPC ......... D21F 7/008; D21F 3/0272; D21F 3/08; D21F 3/10; D21G 1/0093; D21G 7/00
USPC ......... 425/363, 194, 505, 508, 517, 506, 504; 264/119, 284, 299; 34/453, 507; 162/204, 207, 362, 368, 372
See application file for complete search history.

(56) References Cited

U.S. PATENT DOCUMENTS

| 3,238,635 A | 3/1966 | Gravenstreter |
| 3,300,368 A | 1/1967 | Cooper et al. |

(Continued)

FOREIGN PATENT DOCUMENTS

WO   WO 2013/156275   10/2013

OTHER PUBLICATIONS

U.S. Appl. No. 13/774,144, filed Feb. 22, 2013, Miguel Angel Valle, et al.

(Continued)

*Primary Examiner* — Joseph S Del Sole
*Assistant Examiner* — Lawrence D Hohenbrink, Jr.
(74) *Attorney, Agent, or Firm* — Peter D. Meyer

(57) ABSTRACT

An apparatus for the application of atomized fluid to a permeable web material is disclosed. The apparatus has a fluid source and a receipt plenum. The fluid source is disposed in proximate fluid contact with the first surface of the web material. The fluid source has a positively pressured permeable roll having atomized fluid and at least one aperture disposed therein. The apertures provide fluid communication between an inner portion of the roll and a surface thereof. The fluid is disposable from the inner portion to the surface through the apertures into contacting engagement with the permeable web material. The receipt plenum has an opening disposed adjacent to the second surface of the web material that provides a source of negative pressure to the second surface of the web material that causes the fluid to traverse through the web.

20 Claims, 8 Drawing Sheets

(56) References Cited

U.S. PATENT DOCUMENTS

| | | | |
|---|---|---|---|
| 3,587,177 | A | 6/1971 | Overly et al. |
| 3,604,124 | A | 9/1971 | Medley et al. |
| 3,868,215 | A | 2/1975 | Frezza |
| 4,321,760 | A | 3/1982 | Meier |
| 4,529,480 | A | 7/1985 | Trokhan |
| 4,776,107 | A | 10/1988 | Buske |
| 5,455,992 | A | 10/1995 | Kurschatke et al. |
| 5,778,559 | A | 7/1998 | Winhein |
| 5,855,476 | A | 1/1999 | Gottschalk |
| 6,077,590 | A | 6/2000 | Archer et al. |
| 6,125,754 | A | 10/2000 | Harris |
| 6,264,795 | B1 | 7/2001 | Hamel |
| 6,318,727 | B1 | 11/2001 | Hada |
| 6,417,483 | B1 | 7/2002 | Sator |
| 6,553,689 | B2 | 4/2003 | Jain et al. |
| 7,141,142 | B2 | 11/2006 | Burazin et al. |
| 7,413,629 | B2 | 8/2008 | Fisher et al. |
| 7,694,433 | B2 | 4/2010 | Fisher et al. |
| 2003/0201085 | A1* | 10/2003 | Vinson et al. ............ 162/204 |
| 2006/0008514 | A1 | 1/2006 | Koenig et al. |
| 2006/0051516 | A1* | 3/2006 | Pietikainen et al. .......... 427/426 |
| 2006/0111808 | A1* | 5/2006 | Burma ..................... 700/129 |
| 2008/0029234 | A1 | 2/2008 | Latti et al. |
| 2010/0012203 | A1* | 1/2010 | McNeil et al. ............ 137/561 R |

OTHER PUBLICATIONS

Anon, "Another alternative for re-humidifying," Deutscher Drucker, vol. 31 (16), pp. w174 & w176, 2 pages (Apr. 27, 1995)—Abstract.

Barlett, L. C., et al., "Coating of web materials," Research Disclosure, vol. 139 (11), p. 15, 1 page (Nov. 1975).

Cohen, Edward, et al., "Conserve Energy," Paper, Film and Foil Converter, vol. 83 (2), pp. 30-32, 3 pages (Feb. 2009).

Karakourtis, Harry J., "Web Rehumidification and Control," The Journal of the Technical Association of the Pulp and Paper Industry, vol. 55 (7), pp. 1084-1090, 7 pages (Jul. 1972).

Shilova, G.I., et al., "Dyeing Kinetics General Model Having Regard to the Boundary Layer Resistance," Research Institute of Organic Intermediates and Dyes; Institute of Chemical Technology, Ivanovo (1975)—English translation.

Sugihara, Masahiro, et al., "Technologies for High-Speed Coating," Japan Tappi Journal, vol. 55 (12), pp. 39-47, 9 pages (2001)—Abstract.

Sugihara, M., et al., "Control of dynamic wetting line and entrainment of boundary air in high speed curtain coating," Tappi Coating and Graphic Arts Conference Trade Fair—Orlando FL USA, vol. 55 (12), pp. 15-25, 11 pages (May 5-8, 2002)—Abstract.

Tripathi, P., et al., "A study for the statistical optimization of a high speed curtain coater," 2006 TAPPI Papermakers Conference and 2006 TAPPI Coating and Graphic Arts Conference Proceedings—Atlanta GA USA, Session 3, 4 pages (Apr. 24-27, 2006)—Abstract.

Tripathi, P., et al., "A statistical study of process variables to optimize a high speed curtain coater—Part I," Tappi Journal, vol. 8 (1), pp. 20-26, 7 pages (Jan. 2009).

Tripathi, P., et al., "A statistical study of process variables to optimize a high speed curtain coater—Part II," Tappi Journal, vol. 8 (2), pp. 29-32, 4 pages (Feb. 2009).

PCT International Search Report, mailed May 28, 2014, 99 pages.

\* cited by examiner

EQUIPMENT AND PROCESSES FOR THE APPLICATION OF ATOMIZED FLUID TO A WEB SUBSTRATE

FIELD OF THE INVENTION

The present disclosure relates to the introduction of atomized fluids and/or gaseous substances into web substrates to enhance the useful properties and attributes of web substrates and for enhancing the effect of downstream converting operations. More specifically, the present disclosure provides an improved apparatus and process for the application of steam to a cellulose-based web substrate that enhances the effect of downstream embossing operations upon the web substrate.

BACKGROUND OF THE INVENTION

In the manufacture and processing of a moving web material, it is desirable to provide for the introduction of fluids, such as steam, to the web material in order to enhance the effect of various web-handling processes. For example, steam can be used to moisturize a web that has been over dried due to equipment in the web making or web handling process that tend to remove moisture from the web material during handling. It is known that condensation on the web material, due to the impingement of steam thereon, effectively increases the temperature of the web material and its effective moisture content. This is believed to effectively plasticize the web and make it easier and more susceptible to deformation. In addition, steam has been used to improve both the bulk generation and tensile efficiency of such embossing procedures that impart a high definition embossment. Such steam processes have been used in the processing of air laid substrates, single ply wet laid substrates, dual ply wet laid substrates, non-woven substrates, woven fabrics, and knit fabrics.

Numerous processes for the application of steam to a web material are known in the art. For example, parent rolls of creped base sheet materials can be unwound and passed over a steam boom prior to embossing the web material between matched steel embossing rolls. In such a process, high quality steam is supplied to an application boom at anywhere from 5 psi to 10 psi. A typical boom is constructed from stainless steel pipe, capped on one or both ends, that is provided with a plurality of nozzles. The nozzles are capable of providing a spray of steam upon a passing web material as the web material passes proximate to the steam boom. An exemplary process utilizing such an application is described in U.S. Pat. No. 6,077,590.

However, such an application can have significant drawbacks. For example, the steam is applied to the passing web material in an ambient environment. This can allow steam that does not impinge upon the web material to be released to the ambient atmosphere and then condense upon the processing equipment. Such condensation can cause the appearance of rust upon processing equipment. This can then shorten the lifespan of expensive processing equipment. In addition, the impingement of steam upon the passing web material can cause debris resident upon the web material to dislodge. This dislodged debris is then airborne and can be deposited upon the damp processing equipment. Such a collection and buildup of debris increases the risk of product contamination, or otherwise increases the frequency and effort required to clean and maintain the processing equipment. Additionally, not all steam emanating from the stainless steel pipe is effectively deposited upon the passing web material. If one were to consider a steam molecule as a particle, the steam particle, upon release from the steam boom, is provided with sufficient momentum to enable it to rebound off the web material or pass through the web material to the ambient atmosphere surrounding the web material. This does not provide any heating effects upon the web material. This may provide insufficient heat to the web material in order to facilitate any plastic deformation that may be required due to the needs of any downstream processing. In sum, these processes are simply not efficient.

There are other systems for applying steam to a web material that have higher stated efficiencies. However, these systems tend to be unnecessarily complex. For example, some systems provide a pair of dripless steam boxes arranged above and below the plane of a passing web material. The steam boxes are generally closely embraced and enclosed by a steam chamber housing. The steam chamber housing momentarily confines a billowing steam in the immediate vicinity of the web material. Excess steam is removed by way of a downdraft exhaust system. Such steam processing systems are disclosed in U.S. Pat. No. 3,868,215. The incorporation of such complex processing equipment into a web material processing system is generally not financially feasible.

Therefore, it would be advantageous to provide for the application of a fluid, such as steam, to a passing web material in a cost effective and non-complex manner. It is in this way that a web material can be heated and moisturized in order to facilitate plastic deformation. Increasing the ability of a web material to plastically deform facilitates the downstream treatment of the treated web material for embossing, compaction, softening, and contraction.

SUMMARY OF THE INVENTION

The present disclosure provides an apparatus for the application of atomized fluid to a permeable web material having a first surface, a second surface opposed thereto, a machine direction, and a cross-machine direction orthogonal and co-planar thereto.

The apparatus has a fluid source and a receipt plenum. The fluid source is disposed in proximate fluid contact with the first surface of the web material. The fluid source has a positively pressured permeable roll. The positively pressured permeable roll has apertures disposed therein that provide fluid communication between an inner portion of the roll and a surface thereof. The positively pressured permeable roll has atomized fluid disposed therein that is disposable from the inner portion to the surface through the apertures into contacting engagement with the permeable web material.

The receipt plenum has at least one opening disposed adjacent to the second surface of the web material. The receipt plenum provides a source of negative pressure to the second surface of the web material through a portion of the at least one opening opening. The atomized fluid disposed from the fluid source contacts the first surface of the permeable web material and is caused to traverse therethrough by the source of negative pressure. A portion of the atomized fluid contacting the first surface of the web material is then contained by the receipt plenum.

DETAILED DESCRIPTION

Figure 1:
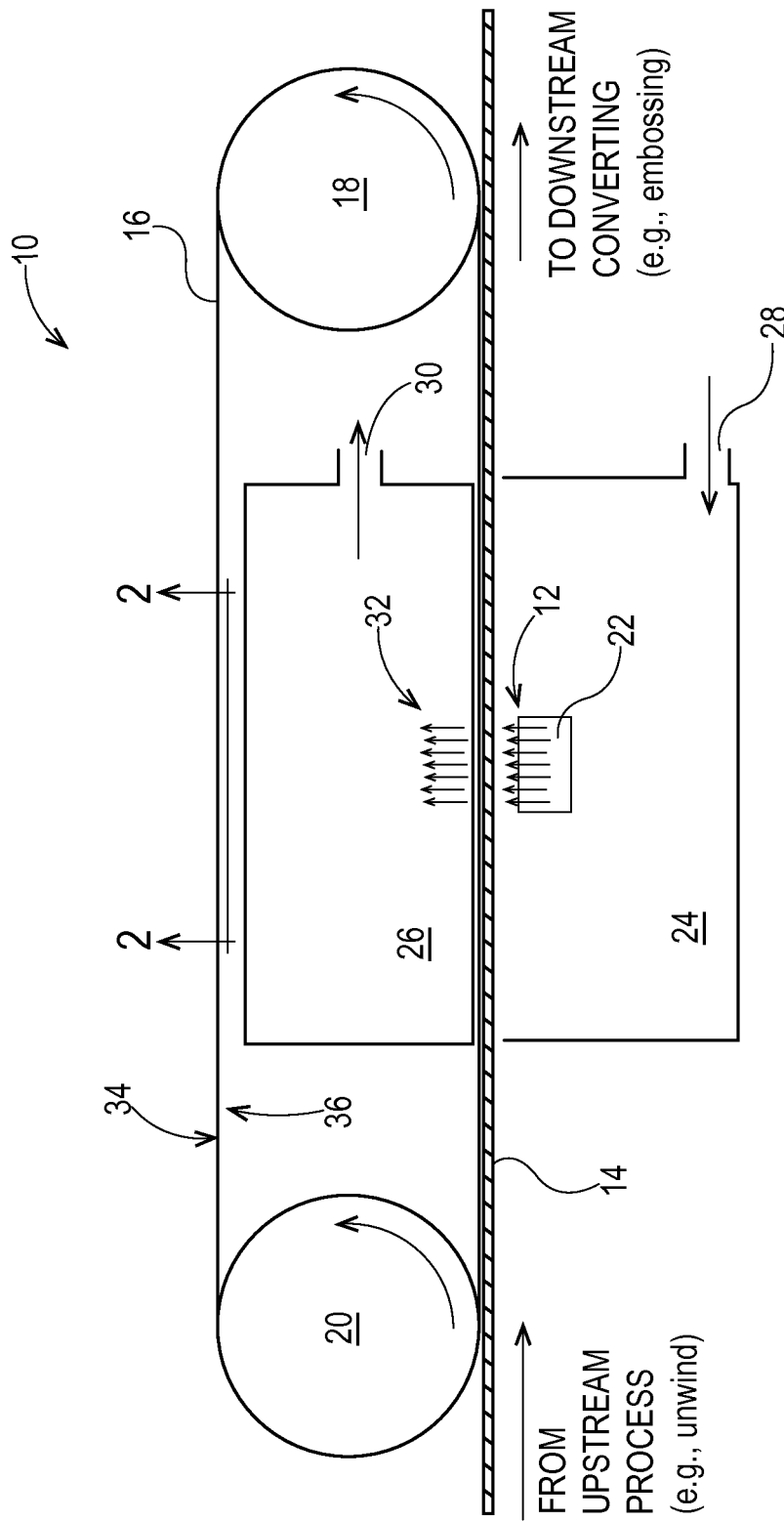
FIG. 1 is a cross-sectional view of an exemplary embodiment of an apparatus for the application of an atomized fluid to a web substrate according to the present description.

It has been discovered that the introduction of a fluid, such as steam, into a web material prior to any processing of the web material can enhance the effect of the downstream process. For example, it is believed that the impingement and ensuing condensation of the steam upon, and/or into, a web material prior to any downstream processing increases both the temperature and moisture content of the web material. Increasing the temperature and/or moisture of a web material can effectively render the web material more susceptible to plastic deformation, thereby making the web material easier to deform. In this regard, it has been found that air foils can be used as a delivery device for the impingement of such a fluid upon, and/or into, such a web material. Using an air foil as a delivery device for such a fluid can maintain intimate contact between the steam and the web material for a period of time sufficient to allow for the condensation of such a fluid onto and into the web material to occur. While it is known that air foils can be effective in the separation of boundary layer air from a high speed web material surface, it was surprisingly found that the introduction of fluids in place of the boundary layer air removed from the web material by the air foil can provide the above-mentioned benefits to the web material.

It should be realized that fluids commensurate in scope for use with the apparatus and process of the present disclosure can be a substance, as a liquid or gas, that is capable of flowing, gasification, and/or sublimation and that changes its shape at a steady rate when acted upon by a force tending to change its shape. Exemplary, but non-limiting, atomizable fluids suitable for use with the present disclosure includes opacifying agents; optical enhancing agents; optical brighteners; surface energy modifiers; inks; dyes; softening agents; cleaning agents; dermatological solutions; wetness indicators; adhesives; botanical compounds (e.g., described in U.S. Patent Publication No. US 2006/0008514); skin benefit agents; medicinal agents; lotions; fabric care agents; dishwashing agents; carpet care agents; surface care agents; hair care agents; air care agents; water, steam, actives comprising a surfactant selected from the group consisting of: anionic surfactants, cationic surfactants, nonionic surfactants, zwitterionic surfactants, and amphoteric surfactants; antioxidants; UV agents; dispersants; disintegrants; antimicrobial agents; antibacterial agents; oxidizing agents; reducing agents; handling/release agents; perfume agents; perfumes; scents; oils; waxes; emulsifiers; dissolvable films; edible dissolvable films containing drugs, pharmaceuticals and/or flavorants. Suitable drug substances can be selected from a variety of known classes of drugs including, for example, analgesics, anti-inflammatory agents, anthelmintics, antiarrhythmic agents, antibiotics (including penicillin), anticoagulants, antidepressants, antidiabetic agents, antipileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, corticosteroids, cough suppressants (expectorants and mucolytics), diagnostic agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anorexics, synpathomimetics, thyroid agents, PDE IV inhibitors, NK3 inhibitors, CSBP/RK/p38 inhibitors, antipsychotics, vasodilators, xanthenes, and combinations thereof.

The fluids capable of integration into the apparatus and process of the present disclosure could provide virtually any desired benefit to a web material. Such a benefit can comprise the appearance, texture, smell, or any other desired, or intended, physical characteristic of the web material. In this regard, fluids commensurate in scope with the present invention can include substantially gaseous substances, such as aerosols, smoke, other particulate-containing fluids, as well as liquids that can be heated to their gaseous form, such as steam, hydrocarbons, water-laden air, other chemical vapors, and the like. While a preferred embodiment of the present invention incorporates the use of steam as a fluid, it should be understood that a reference to steam is inclusive of any fluid or combinations of fluids, and/or vapors suitable for use with the present invention as discussed supra.

Web materials having an increased susceptibility to plastic deformation can demonstrate an improved embossment appearance for any given embossment design and appropriate depth of engagement. In other words, the addition of a small amount of moisture to a web material by the application of steam can increase the amount of stretch in the web material thereby allowing for a better embossment appearance. This can be particularly true with wet laid and air laid substrates that have been embossed with a deep nested embossing process.

TABLE 1

Exemplary CD Dry Tensile Efficiencies for Non-Steam Enhanced and Steam Enhanced Wet Laid Cellulose

| Steam (On/Off) | Depth of Engagement (mils) | CD Dry Tensile Strength (g/in) | Deformation Height (microns) |
| --- | --- | --- | --- |
| Off | 95 | 692 | 781 |
| On | 95 | 709 | 1012 |
| Off | 110 | 585 | 939 |
| On | 110 | 665 | 1255 |

As can be seen from Table 1, the application of steam to a wet laid cellulose web material prior to deep nested embossing can provide the finally embossed cellulose web material with a higher deformation height having a higher cross-machine direction (CD) dry tensile efficiency than a similar cellulose web material not treated with steam. By convention and as should be known to those of skill in the art, CD dry tensile efficiencies are generally used as a measure of web strength because wet-laid substrates are known to have less CD stretch than machine-direction (MD) stretch. Thus, as was found and summarized in Table 1, the application of steam to the web material prior to such an embossing step can provide additional stretch (i.e., tensile efficiency) to the web material.

Without desiring to be bound by theory, it is believed that the application of steam to a cellulose web material causes an increase in both the moisture content and effective temperature of the treated web material. This causes the cellulose web material to move from the region indicated on the graph as elastic (i.e., where the fiber tends to exhibit behavior typical elastic-like behavior) to the region where the cellulose substrate is capable of plastic deformation. This is typical for many cellulose materials and can be found in references including J. Vreeland, et al., Tappi Journal, 1989, pp. 139-145.

FIG. 1 depicts an exemplary apparatus 10 for the application of a fluid stream 12 (e.g., steam, lotion, softeners, etc.) to a web material 14 suitable for use with a downstream web material converting process such as an embossing apparatus (not shown). Web material 14 (e.g., tissue paper web, paper web, web, paper sheet, and paper product) is used generally to refer to sheets of paper made by a process comprising the steps of forming an aqueous papermaking furnish, depositing this furnish on a foraminous surface, such as a Fourdrinier wire, and removing the water from the furnish (e.g., by gravity or vacuum-assisted drainage), forming an embryonic web, transferring the embryonic web from the forming surface to a transfer surface traveling at a lower speed than the forming surface. The web is then transferred to a fabric upon which it is through air dried to a final dryness after which it is wound upon a reel.

Web material 14 is considered to be an association of fibrous elements that together form a structure, such as a unitary structure, capable of performing a function and is intended to include fibrous structures, absorbent paper products, and/or products containing fibers. Web material 14 may be homogeneous, layered, and/or co-formed.

Other materials are also intended to be within the scope of the present invention as long as they do not interfere or counter act any advantage presented by the instant invention. Suitable web materials may include cloth, knitted, wovens or nonwovens, paper, cellulose fiber sheets, laminates, high internal phase emulsion foam materials, and combinations thereof. The properties of a selected deformable material can include, though are not restricted to, combinations or degrees of being: porous, non-porous, microporous, gas or liquid permeable, non-permeable, hydrophilic, hydrophobic, hydroscopic, oleophilic, oleophobic, high critical surface tension, low critical surface tension, surface pre-textured, elastically yieldable, plastically yieldable, electrically conductive, and electrically non-conductive. Such materials can be homogeneous or composition combinations.

Web material 14 also includes products suitable for use as packaging materials. This may include, but not be limited to, polyethylene films, polypropylene films, liner board, paperboard, cartoning materials, and the like. Additionally, web material 14 may include absorbent articles (e.g., diapers and catamenial devices). In the context of absorbent articles in the form of diapers, web material 14 may be used to produce components such as backsheets, topsheets, landing zones, fasteners, ears, side panels, absorbent cores, and acquisition layers. Descriptions of absorbent articles and components thereof can be found in U.S. Pat. Nos. 5,569,234; 5,702,551; 5,643,588; 5,674,216; 5,897,545; and 6,120,489; and U.S. Patent Publication Nos. 2010/0300309 and 2010/0089264. Also included within the scope of web material 14 are products suitable for use as packaging materials. This may include, but not be limited to liner board, paperboard, cartoning materials, and the like.

The web materials 14 of the present invention may contain or be comprised entirely of various types of polymers such as hydroxyl polymers (e.g., polyols, such as polyvinyl alcohol, polyvinyl alcohol derivatives, polyvinyl alcohol copolymers, starch, starch derivatives, starch copolymers, chitosan, chitosan derivatives, chitosan copolymers, cellulose, cellulose derivatives such as cellulose ether and ester derivatives, cellulose copolymers, hemicellulose, hemicellulose derivatives, hemicellulose copolymers, gums, arabinans, galactans, proteins and various other polysaccharides and mixtures thereof), non-thermoplastic polymers, thermoplastic polymers (e.g., polyolefins, polyesters, copolymers thereof, and mixtures thereof), biodegradable polymers (e.g., hydroxyl polymers described above, polylactic acid, polyhydroxyalkanoate, polycarprolactone, polyesteramides and other biodegradable polymers known in the art, and mixtures thereof), non-biodegradable polymers, and mixtures thereof.

Web material 14 can be used to produce sanitary tissue products that are generally described as one or more fibrous structures, converted or not, that are useful as a wiping implement for post-urinary and post-bowel movement cleaning (bath tissue), for otorhinolaryngological discharges (facial tissue and/or disposable handkerchiefs), and multi-functional absorbent and cleaning uses (absorbent towels and/or wipes).

Returning again to FIG. 1, the apparatus 10 provides for the web material 14 to be unwound from a parent roll (not shown), or otherwise originate from a calendaring operation (not shown), slitter (not shown), or any desired upstream process. The apparatus 10 generally includes fluid source 22 (or optionally—includes source plenum 24 having fluid source 22 residing therein), receipt plenum 26 disposed adjacent and in proximate fluid contact with source plenum 24, and permeable belt 16 rotating about first roller 18 and second roller 20. Permeable belt 16 preferably traverses a region disposed between source plenum 24 and receipt plenum 26. In other words, a permeable belt 16 having a first side 34 and a second side 36 traverses the opening between source plenum 24 and receipt plenum 26 so that a fluid originating within source plenum 24 migrates from source plenum 24 through permeable belt 16 from the first side 34 to second side 36 and into receipt plenum 26.

A web material 14 is then positioned into contacting engagement with the first side 34 of permeable belt 16 so that a fluid stream 12 emanating from fluid source 22 can be brought into contacting engagement with the web material 14 as it passes through the region disposed between source plenum 24 and receipt plenum 26. Without desiring to be bound by theory, it is believed that a fluid stream 12 released from fluid source 22 can impinge upon the surface of web material 14 as it is disposed upon the first side 34 of permeable belt 16, migrate through web material 14 and permeable belt 16 into receipt plenum 26. Further, without desiring to be bound by theory, it is also believed that a portion of fluid stream 12 released from fluid source 22 will become entrapped within the interstices of web material 14 and/or experience a phase change as it migrates therethrough. Thus, only a portion of the fluid stream 12 released from fluid source 22 will enter receipt and 26 while the remainder ensnared within web material 14 enhances the effect of any downstream converting operations performed upon web material 14.

It is believed that the constituents of fluid stream 12 entrapped within web material 14 are provided with a residence time within web material 14 that is equivalent to the MD distance disposed between apparatus 10 and any downstream converting operations (not shown). In theory, web material 14 (such as air laid substrates, single ply substrates, multiple-ply substrates, wet laid substrates, non-woven substrates, woven fabrics, knit fabrics, and combinations thereof) can then be treated in any downstream operation (not shown) including but not limited to rubber-to-steel embossing, matched steel embossing, deep nested embossing, compaction, softening, micro-contraction, and combinations thereof.

Fluid stream 12 can be provided in any configuration required for the envisioned downstream converting process. For example, fluid stream 12 can be provided as a steam header that provides a uniform steam 'blanket' across the entirety of the web material 14. Alternatively, fluid stream 12 can be provided as a plurality of discrete units that provide a source of steam to only a desired portion of the web material 14. In other words, the fluid stream 12 can originate from a fluid source that comprises a plurality of individual fluid sources, each configured to only provide for the impingement of the fluid upon a designated or desired portion of web material 14. Such a configuration could provide for a plurality of fluid 'lines' to be provided in the MD of web material 14. One of skill in the art could provide for virtually any desired arrangement of fluid sources within the scope of the apparatus 10 that can provide for any desired pattern of fluid to ultimately be disposed upon web material 14.

The exhaust 30 of receipt plenum 26 is provided with a source of lower pressure (e.g., negative pressure) in order to provide a pressure gradient that can provide any necessary impetus for the constituents of fluid stream 12 to migrate from source plenum 24 through web material 14 permeable belt 16 and into receipt and 26. Exemplary sources of forming a pressure gradient such as a lower pressure, hereinafter "negative pressure" may include but not be limited to vacuum pumps, fans, blowers, turbines, and the like. In any regard it is desirable to provide a significant enough source of negative pressure from receipt and 26 upon the second side 36 of permeable belt 16 so that the constituents of fluid stream 12 originating in source plenum 24 are drawn through web material 14 and through permeable belt 16 within the time that an identified portion of web material 14 traverses the region disposed between source plenum 24 and receipt plenum 26.

Receipt plenum 26 can be provided in any configuration required for the envisioned downstream converting process. For example, receipt plenum 26 can be configured to provide for the collection of rogue fluid 32 uniformly across the entirety of the web material 14. Alternatively, receipt plenum 26 can be provided as a plurality of discrete units that provide for the collection of rogue fluid 32 at only a desired portion of the web material 14. In other words, the fluid stream 12 can be configured to provide either a 'continuous blanket' or be configured to provide for the impingement of the fluid upon a designated or desired portion of web material 14 and receipt plenum 26 can be configured to collect rogue fluid 32 only at discrete positions located across the CD of web material 14. Such a configuration could also provide for a plurality of fluid 'lines' to be provided in the MD of web material 14. One of skill in the art could provide for virtually any desired arrangement of fluid sources within the scope of the apparatus 10 that can provide for any desired pattern of fluid to ultimately be disposed upon web material 14.

Figure 2:
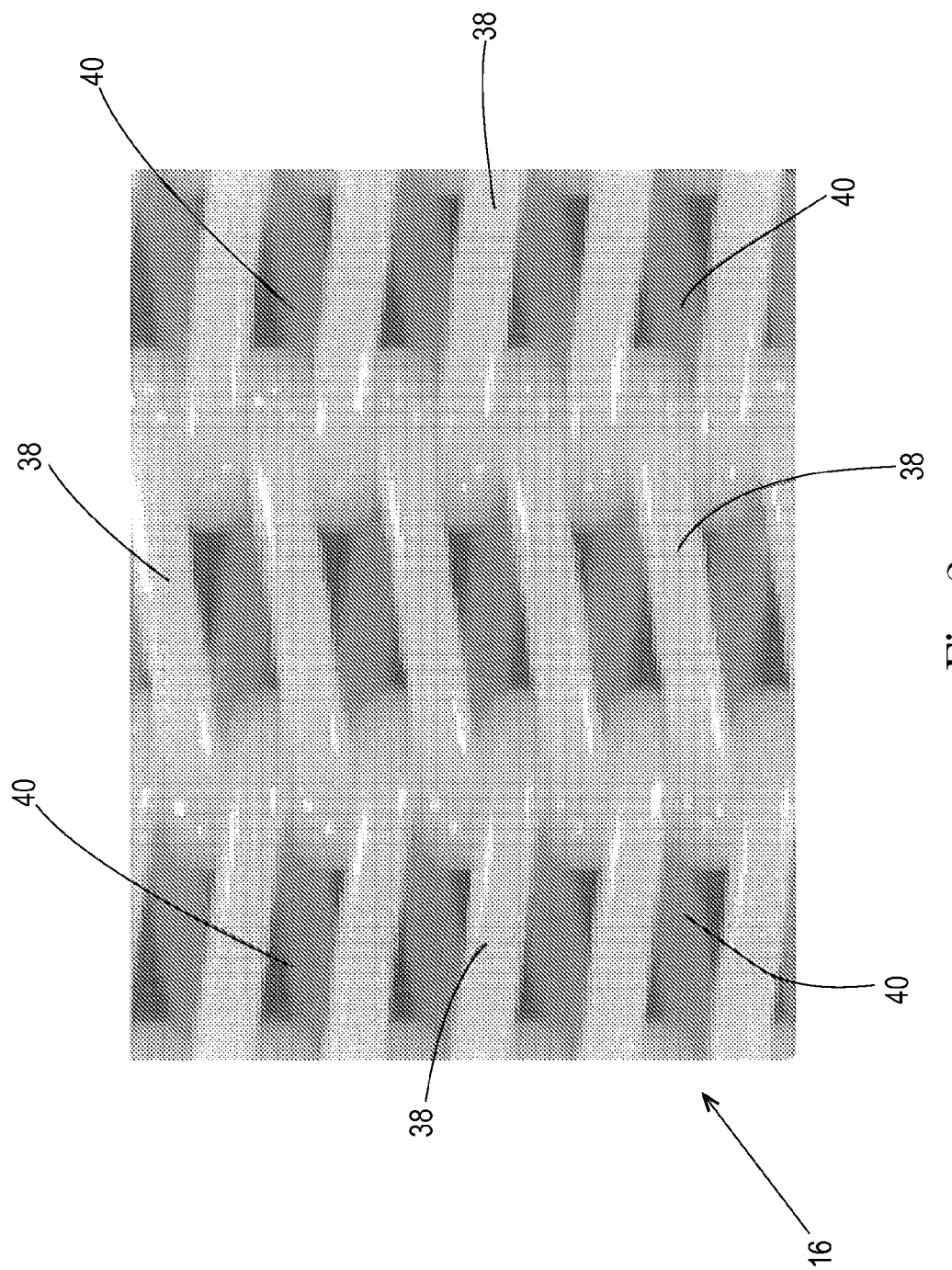
FIG. 2 is a plan view of an exemplary permeable belt suitable for use with the described apparatus and taken along the line 2-2 of FIG. 1.

Referring now to FIG. 2, the photo micro-graphic plan view of an exemplary permeable belt 16 is shown. An exemplary permeable belt 16 is provided as a foraminous woven member. The permeable belt 16 is provided as a continuous loop of web material that traverses past the region disposed between source and 24 and receipt 26 as it revolves around first roller 18 and second roller 20. The permeable belt 16 can be formed from any material, including but not limited any known polymers, metals, and combinations thereof and provided with any form of construction and/or weave that provides the permeability desired. A suitable permeable belt 16 is disclosed in U.S. Pat. No. 4,529,480.

A preferred permeable belt 16 suitable for use with the apparatus 10 of the present disclosure is provided as a foraminous woven member work. The utilization of the permeable belt 16 in the presently described apparatus 10 can provide support for web materials 14 as the web material 14 traverses the region disposed between source plenum 24 and receipt plenum 26. One of skill in the art will understand that web materials 14 suitable for use with and likely to be utilized with the apparatus 10 of the present disclosure typically have low basis weight, relatively low caliper, relatively low strength compared to non-absorbent paper products, high softness, and relatively high absorption. The described web materials 14 are therefore sensitive to manipulations performed by equipment suitable for use in conjunction with the present apparatus 10. By way of example web materials 14 believed to be suitable for use with the present apparatus 10 may include bath tissue, facial tissue, and paper toweling.

A permeable belt 16 can be characterized by having two physically distinct regions distributed across its surfaces. One region is a continuous network 38 region which has a relatively high density and high intrinsic strength. The other region is one which is comprised of a plurality of openings 40 that are completely encircled by the network region. The openings 40 in the latter region have relatively low densities, higher permeability, and relatively low intrinsic strength compared to the continuous network 38 region.

Exemplary permeable belts 16 can have a mesh ranging from about 9×9 to about 17×11 to about 16×5. Exemplary permeable belts 16 can be a single layer, a stuffed spiral, or a spiral fabric where the machine direction strands are 0.029 inch to about 0.031 inch polyester and the cross machine direction strands are 0.031 inch to about 0.036 inch polyester. The air permeability of an exemplary permeable belt 16 can range from about 385 cfm/ft$^2$ to about 1400 cmf/ft$^2$, have an open area ranging from about 16.5% to about 51.3%, and a caliper ranging from about 0.071 inches to about 0.099 inches. The frame size of an exemplary permeable belt 16 can be from about 0.029 inches×0.030 inches to about 0.080 inches×0.080 inches to about 0.164 inches×0.034 inches. Exemplary permeable belts 16 can have a fiber support index ranging from about 17.3 to about 26.0 and a drainage index ranging from about 4.2 to about 12.6. Exemplary permeable belts 16 suitable for use with the present description are the SpiralTuf™ permeable belts available from AstenJohnson, Montreal, Canada.

Referring again to FIG. 1, and as stated supra, transport of the constituents comprising fluid stream 12 from the source plenum 24 through web material 14, permeable belt 16 and into receipt plenum 26 is accomplished by inducing a pressure gradient. The pressure gradient is generally created by a mechanical device such as a pump, a blower and/or a fan. The mechanical device that induces the pressure gradient is preferably in fluid communication with receipt 26. Therefore, the pressure gradient can assist the mass flow of the constituents comprising fluid stream 12 from start to finish. Those skilled in the art may also recognize the pressure gradients can also be derived from density gradients of gas phase components.

In accordance with the present disclosure, it is preferred that the total mass flow of the fluid stream 12 be closely matched to the emission rate of the fluid stream 12 from fluid source 22. The need for any makeup air to complete the total volumetric flow rate through the apparatus 10 can be provided as dilution air through inlet 28 located in source plenum 24. In any regard it is preferred that the total volumetric flow rate through the apparatus 10 remain consistent throughout the processing of web material 14 due to the physical and intrinsic properties of the web material 14 discussed infra. Without desiring to be bound by theory, it is believed that if the total volumetric flow rate to the apparatus 10 is not consistent throughout the processing of a web material 14, web material 14 may suffer catastrophic failure resulting in a shutdown of the manufacturing operation for the web material 14. It is believed that providing permeable belt 16 in a fashion discussed supra, inconsistencies in the total volumetric flow rate through the apparatus 10 can be minimized and result in negligible or no detrimental effects to web material 14. In the event source plenum 24 is not provided (i.e., it is optional), then any make-up air required by apparatus 10 would necessarily be provided by the surrounding environment.

The source plenum 24 and receipt plenum 26 of the present invention are preferably positioned in close proximity to each other and to permeable belt 16 and web material 14 disposed thereon in order to minimize the region disposed between source plenum 24 and receipt plenum 26. The spatial distance between the proximate portions of source plenum 24 and receipt plenum 26 is preferably a substantially uniform. In any regard, the apparatus 10 is preferably operated at a pressure gradient so that the fluid stream 12 is pulled into receipt plenum 26. To minimize the region disposed between source plenum 24 and receipt plenum 26, mechanical features, such as extensions may be added to source plenum 24 and/or receipt plenum 26. Any extension provided to source plenum 24 and/or receipt plenum 26 may also provide side seals that contactingly engage second side 36 of permeable belt 16 (receipt plenum 26) and seals that contactingly engage the first side 34 of permeable belt 16/web material 14 (source plenum 24).

In accordance with the present disclosure, it is preferred that the apparatus 10 total mass flow closely matches the generation rate of fluid stream 12. In other words, the total volumetric flow rate from the source plenum 24 can preferably be at least about 100% of the volumetric flow of the fluid stream 12. Additionally, the apparatus 10 of the present disclosure should be capable of achieving substantially uniform flow across entire portion of the permeable belt 16 and web material 14 disposed thereon while that portion of the permeable belt 16 and web material 14 disposed thereon is disposed within the region between source plenum 24 and receipt plenum 26. This may be achieved when a head space is present in the receipt plenum 26 disposed above that portion of the permeable belt 16 disposed within the region between source plenum 24 and receipt plenum 26. As such, the pressure drop laterally in the head space is preferably negligible with respect to the pressure across the permeable belt 16 and web material 14 disposed thereon. One skilled in the art will recognize that the head space and size of openings 40 disposed within permeable belt 16 may be adjusted to adjust the flow rate across the inlet of receipt plenum 26.

A seal may be provided at the entry and exit points of the permeable belt 16 and web material 14 disposed thereon from the region disposed between source plenum 24 and receipt plenum 26 to prevent any portion of fluid stream 12 or rogue fluid 32 from exiting the entry and exit points of the permeable belt 16 and web material 14 disposed thereon from the region between source plenum 24 and receipt plenum 26. The seal could include either a forced gas or a mechanical seal (not shown). An exemplary mechanical seal may be utilized for retaining fluid stream 12 or rogue fluid 32 from exiting the entry and exit points of the permeable belt 16 and web material 14 disposed thereon from the region between source plenum 24 and receipt plenum 26. If such a seal were constructed of a flexible material, the flexible seal could drag on the permeable belt 16 and/or the web material 14. In any regard, the smaller the distance between the components of the apparatus 10 disposed within the region disposed between source plenum 24 and receipt plenum 26 and the smaller the distance between the source plenum 24 and receipt plenum 26 themselves, the more effective the apparatus 10 will be in providing its intended purpose of entrapping a larger portion of fluid stream 12 within web material 14 when it is disposed within the region disposed between source plenum 24 and receipt plenum 26. Additionally, those skilled in the art recognize that any provided seal could be retractable and such retraction could be automated and controlled for known upsets such as splices or applied coatings, or differing web materials 14.

It is also believed that the apparatus 10 of the present disclosure can utilize a supporting mechanism for securing the permeable belt 16 and/or the web material 14 in close proximity to the region disposed between source plenum 24 and receipt plenum 26. As such, conventional material handling systems and devices are suitable for use with the present invention. The source plenum 24 and receipt plenum 26 can be constructed of conventional materials and may be designed to meet specific application standards. The chamber may exist as a stand-alone device or it may be placed in an enclosed environment, such as, for example, an oven enclosure.

Figure 3:
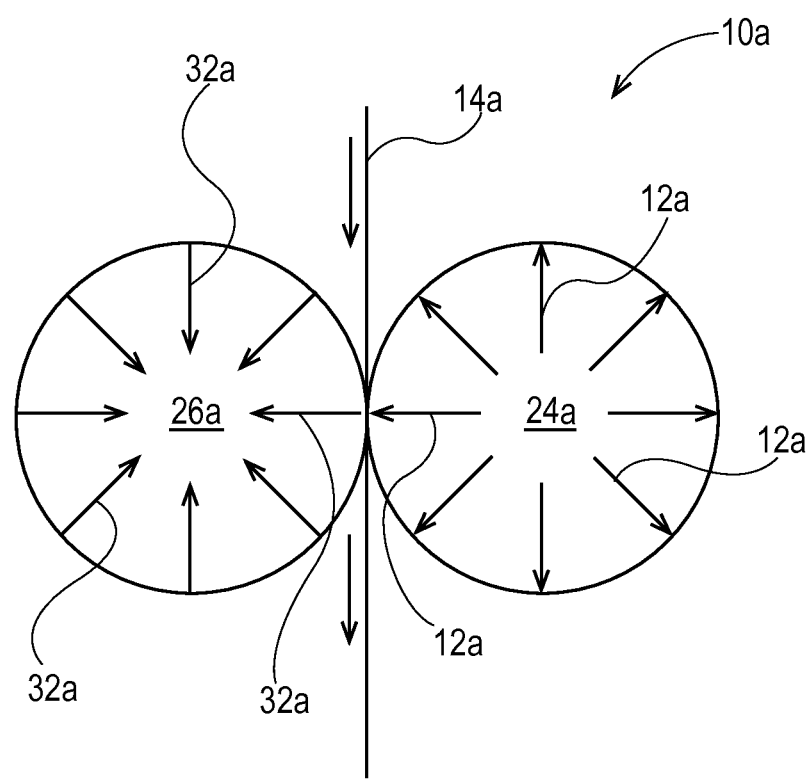
FIG. 3 is a cross-sectional view of an alternative embodiment of an apparatus for the application of an atomized fluid to a web substrate.

As shown in FIG. 3, an alternative embodiment of the present disclosure provides for an apparatus 10a for the application of a fluid stream 12a (e.g., steam, lotion, softeners, etc.) to a web material 14a suitable for use with a downstream web material converting process such as an embossing apparatus (not shown). The apparatus 10a generally includes a source plenum in the form of a positively-pressured permeable roll 24a having fluid stream 12a residing therein and a receipt plenum in the form of a negatively-pressured permeable roll 26a disposed adjacent and in contacting engagement thereto. In other words, a web material 14a traverses the nip formed between a positively-pressured permeable roll 24a having fluid stream 12a residing therein (or otherwise provided internally thereto) and a negatively-pressured permeable roll 26a so that a fluid originating within positively-pressured permeable roll 24a migrates from the source positively-pressured permeable roll 24a through web material 14a and into the negatively-pressured permeable roll 26a. In other words, all that is necessary for apparatus 10a to function sufficiently is the presence of a pressure gradient between the source plenum and receipt plenum provided.

Again, without desiring to be bound by theory, it is believed that a fluid stream 12a released from positively-pressured permeable roll 24a can directly impinge upon the surface of web material 14a as it traverses the nip formed between positively-pressured permeable roll 24a and negatively-pressured permeable roll 26a. Without desiring to be bound by theory, it is also believed that a portion of fluid stream 12a released from positively-pressured permeable roll 24a will become entrapped within the interstices of web material 14a as it migrates therethrough. Thus, only a portion of the fluid stream 12a released from positively-pressured permeable roll 24a will enter negatively-pressured permeable roll 26a while the remainder ensnared within web material 14a enhances the effect of any downstream converting operations performed upon web material 14a such as rubber-to-steel embossing, matched steel embossing, deep nested embossing, compaction, softening, micro-contraction, and combinations thereof.

An alternative embodiment for the treatment of a web material 14a with fluid stream 12a shown in FIG. 3 includes the use of a positively-pressured permeable roll 24a having apertures in selected locations. The positively-pressured permeable roll 24a may be positioned such that the web material 14a contacts at least a portion of the circumferential surface of positively-pressured permeable roll 24a. Positively-pressured permeable roll 24a may be driven by means known in the art such that its surface speed substantially matches the speed of the web material 14a. Fluid stream 12a may be supplied to the interior of positively-pressured permeable roll 24a by piping and rotary unions known in the art. The pressure of fluid stream 12a may be controlled to a desired target in positively-pressured permeable roll 24a. The apertures on the surface of positively-pressured permeable roll 24a may be formed by drilling holes of a desired size and the holes may be located in desired locations on the circumferential surface of positively-pressured permeable roll 24a. The number of holes drilled and the location of the holes may be selected to create a desired pattern.

The pattern of the holes disposed upon positively-pressured permeable roll 24a may determine the pattern of fluid stream 12a application. This pattern may be selected to correspond to a pattern of features in the web material 14a, including but not limited to embossments, regions of indicia, perforations, and the like. The pattern of fluid stream 12a application to the web material 14a may also be selected to correspond to other product features including embossing, printing, perforations, combinations thereof, and the like. The circumferential and axial positions of positively-pressured permeable roll 24a may be controlled by means known in the art such that the pattern of fluid stream 12a application is registered to the web material 14a features. Alternatively, the surface apertures may be any desired shape and size, including non-circular and irregular shapes, and created using laser machining or other suitable material removal means. It has been found that such patterned means of fluid stream 12a application are surprisingly effective in improving product features such as emboss depth and clarity while preserving web material 14a flexibility and softness, which may be compromised when applying fluid stream 12a to the entirety of web material 14a.

Figure 4:
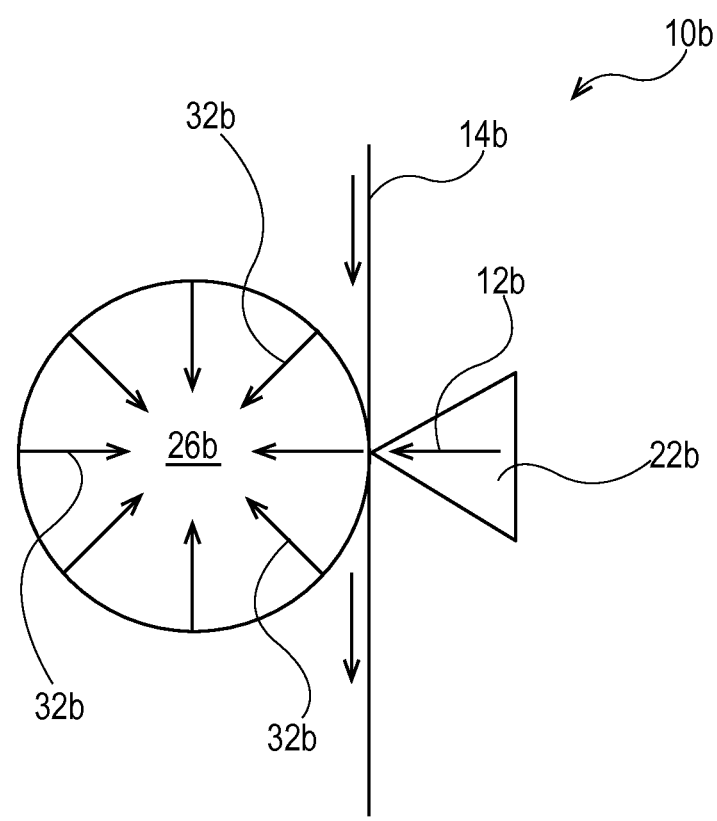
FIG. 4 is a cross-sectional view of another alternative embodiment of an apparatus for the application of an atomized fluid to a web substrate.

As shown in FIG. 4, an alternative embodiment of the present disclosure provides for an apparatus 10b for the application of a fluid stream 12b (e.g., steam, lotion, softeners, etc.) to a web material 14b suitable for use with a downstream web material converting process such as an embossing apparatus (not shown). The apparatus 10b generally includes a fluid source 22b and a receipt plenum in the form of a negatively-pressured permeable roll 26b disposed adjacent thereto. In other words, a web material 14b tangentially traverses the surface of negatively-pressured permeable roll 26b between fluid source 22b and negatively-pressured permeable roll 26b so that a fluid originating within fluid source 22b migrates from the fluid source 22b through web material 14b and into negatively-pressured permeable roll 26b.

Again, without desiring to be bound by theory, it is believed that a fluid stream 12b released from fluid source 22b can directly impinge upon the surface of web material 14b as it traverses between fluid source 22b and negatively-pressured permeable roll 26b. Without desiring to be bound by theory, it is also believed that a portion of fluid stream 12b released from fluid source 22b will become entrapped within the interstices of web material 14b as it migrates therethrough. Thus, only a portion of the fluid stream 12b released from fluid source 22b will enter negatively-pressured permeable roll 26b while the remainder ensnared within web material 14b enhances the effect of any downstream converting operations.

Figure 5:
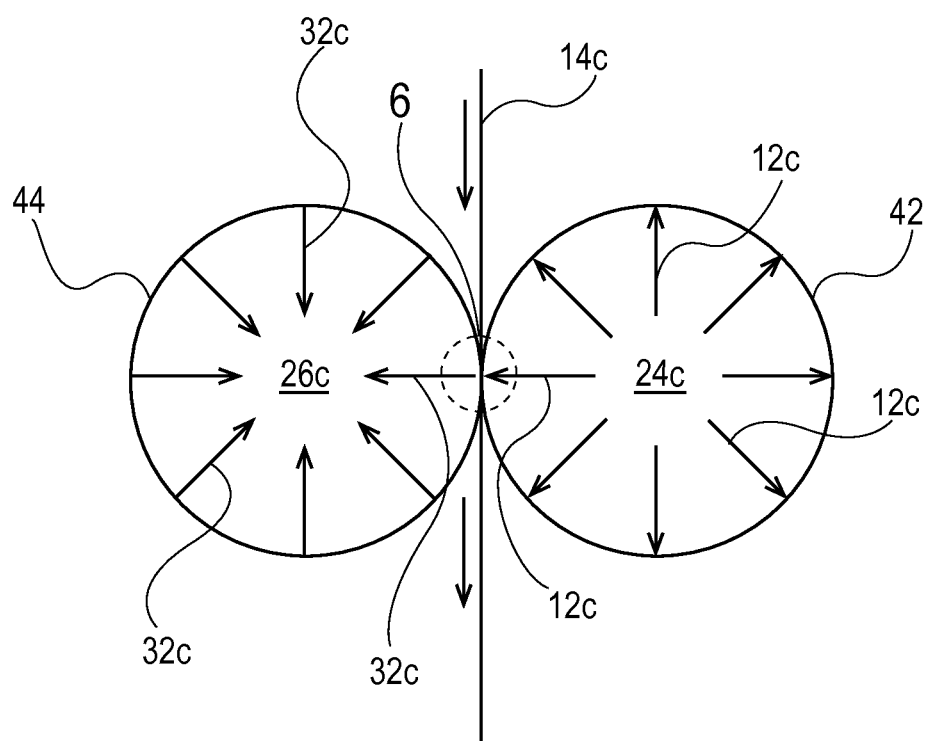
FIG. 5 is a cross-sectional view of still another alternative embodiment of an apparatus for the application of an atomized fluid to a web substrate.
Figure 6:
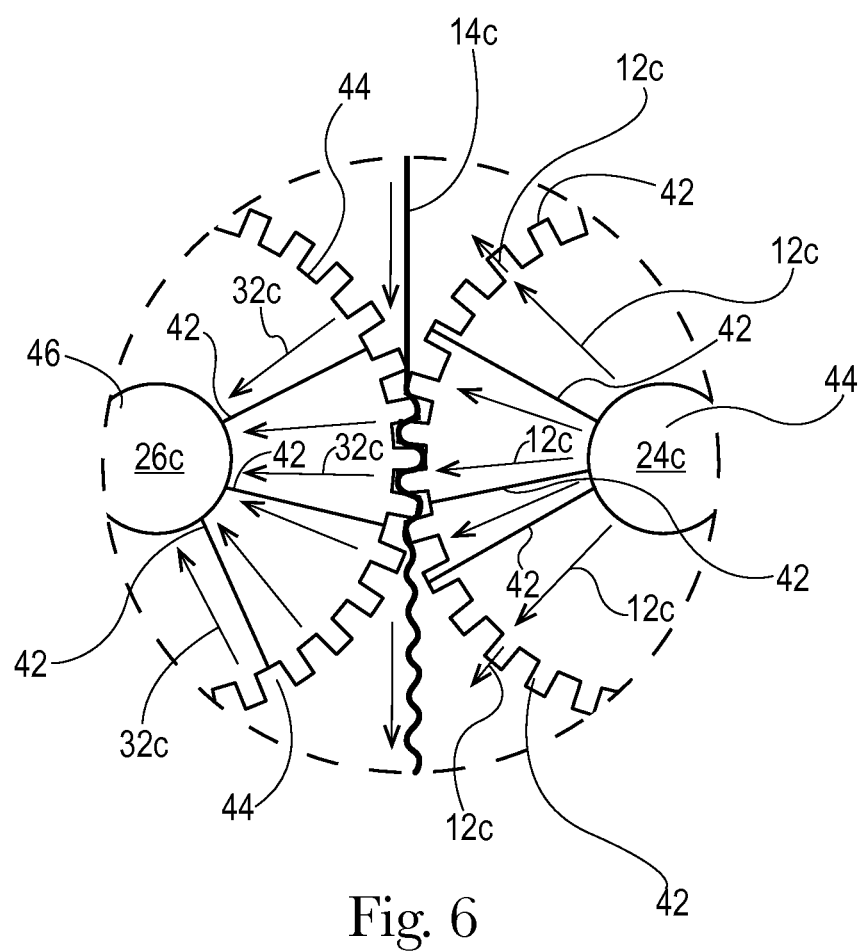
FIG. 6 is an expanded view of the region labeled 6 in FIG. 5.

As shown in FIGS. 5 and 6, an alternative embodiment of the present disclosure provides for an apparatus 10c for the application of a fluid stream 12c as described above to a web material 14c. In the embodiment shown, the fluid stream 12c application to the web material 14c can be provided in a manner integral with a converting process. As shown, the converting process is a pair of embossing rolls 24c, 26c.

Generally described, a typical embossing process consists of a web being fed through a nip formed between juxtaposed generally axially parallel rolls. Embossing elements on the rolls compress and/or deform the web. If a multi-ply product is being formed, two or more plies are fed through the nip and regions of each ply are brought into a contacting relationship with the opposing ply. The embossed regions of the plies may produce an aesthetic pattern and provide a means for joining and maintaining the plies in face-to-face contacting relationship.

Embossing is typically performed by one of three processes; knob-to-knob embossing, nested embossing, or rubber-to-steel embossing. Knob-to-knob embossing typically consists of generally axially parallel rolls juxtaposed to form a nip between the embossing elements on opposing rolls. Nested embossing typically consists of embossing elements of one roll meshed between the embossing elements of the other roll. Examples of knob-to-knob embossing and nested embossing are illustrated in U.S. Pat. Nos. 3,414,459; 3,547,723; 3,556,907; 3,708,; 3,738,905; 3,867,225; 4,483,728; 5,468,323; 6,086,715; 6,277,466; 6,395,133 and 6,846,172 B2.

Knob-to-knob embossing generally produces a web comprising pillowed regions which can enhance the thickness of the product. However, the pillows have a tendency to collapse under pressure due to lack of support. Consequently, the thickness benefit is typically lost during the balance of the converting operation and subsequent packaging, diminishing the quilted appearance and/or thickness benefit sought by the embossing.

Nested embossing has proven in some cases to be a more desirable process for producing products exhibiting a softer, more quilted appearance that can be maintained throughout the balance of the converting process, including packaging. With nested embossing of a multi-ply product, one ply has a male pattern, while the other ply has a female pattern. As the two plies travel through the nip of the embossing rolls, the patterns are meshed together. Nested embossing aligns the knob crests on the male embossing roll with the low areas on the female embossing roll. As a result, the embossed sites produced on one ply provide support for the embossed sites on the other ply.

In rubber-to-steel embossing, only one of the rollers is engraved, while the other roller is covered with a elastic material like rubber. The surface of the elastic material is smooth, except while it is being pressed against the engraved roller in the embossing nip. Elastic recovery to its original smooth shape is extremely rapid. The surface of the engraved roller must be hard enough and durable enough to deform not only the paper that is being embossed, but also must deform the elastic material of the opposing roller (which requires much more force and energy than the paper does). Traditionally, the engraved surface has been steel and the deformable surface has been rubber. However, the engraved roller could have a laser engraved surface made of very hard rubber, while the smooth roller could have a surface made of an elastomeric plastic.

Deep-nested embossing (another type of embossing) has been developed and used to provide unique characteristics to the embossed web. Deep-nested embossing refers to embossing that utilizes paired emboss elements, wherein the protrusions from the different embossing elements are coordinated such that the protrusions of one embossing element fit into the space between the protrusions of the other embossing element. Although many deep-nested embossing processes are configured such that the embossing elements of the opposing embossing members do not touch each other or the surface of the opposing embossing member, embodiments are contemplated wherein the deep-nested embossing process includes tolerance such that the embossing elements touch each other or the surface of the opposing embossing member when engaged. (Of course, in the actual process, the embossing members generally do not touch each other or the opposing embossing member because the web is disposed between the embossing members.) Exemplary deep-nested embossing techniques are described in U.S. Pat. Nos. 5,686,168 and 5,294,475.

Returning again to FIGS. 5 and 6, the outer surface of the described source plenum in the form of embossing roll 24c is preferably fabricated so that the individual emboss knobs are permeable via openings disposed within the tops of the embossments that ostensibly allow the fluid stream 12c to be fed from an underlying shaped fluid reservoir 44 to the dispersal point of fluid stream 12c from the embossment through channels 42. Similarly, the outer surface of the described receipt plenum in the form of embossing roll 26c is preferably fabricated so that the individual emboss recesses are permeable via openings disposed within the bottoms of the embossments that ostensibly allow the fluid stream 12c to be directed toward an underlying source of negative pressure (vacuum source 46) for collection of the remainder of fluid stream 12c (i.e., rogue fluid 32c) from the embossment through channels 42.

One of skill in the art will appreciate that such openings and channels 42 provided in the embossing rolls 24c, 26c could be made via laser drilling or any other suitable means after the individual embossments provided on embossing rolls 24c, 26c are formed. Each embossing roll 24c, 26c may be manufactured as a single roll or by assembled sleeve sections in order to provide flexibility for changing the desired embossing pattern. As such, the surface of a patterned gravure embossing roll 24c, 26c transfers the embossing image directly onto the web material 14c.

In practice, a desired fluid stream 12c such as steam may be fluidly communicated through a rotary union to reservoir 44 provided as a distribution manifold for distribution into individual channels 42. The fluid stream 12c contacts web material 14c through a pore disposed distal upon the embossment disposed upon the surface of embossing roll 24c. One of skill will understand that the pore disposed upon the embossment may be sized as required as would be known to those of skill in the art. This enables the application of the desired quantity of fluid stream 12c upon the surface of web material 14c. The fluid stream 12c is then placed in fluid contact with a passing web substrate 14c through the emboss element disposed upon the surface of embossing roll 24c.

The web material 14c traverses the nip formed between the positively pressured embossing roll 24c having fluid stream 12c residing therein (or otherwise provided internally thereto) and a negatively-pressured embossing roll 26c so that a fluid originating within positively-pressured embossing roll 24c migrates from the source positively-pressured embossing roll 24c through web material 14c and into negatively-pressured embossing roll 26c. Again, without desiring to be bound by theory, it is believed that a fluid stream 12c released from positively-pressured embossing roll 24c can directly impinge upon the surface of web material 14c as it traverses the nip formed between positively-pressured embossing roll 24c and the negatively-pressured embossing roll 26c. Without desiring to be bound by theory, it is also believed that a portion of fluid stream 12c released from positively-pressured embossing roll 24c will become entrapped and/or experience a phase change within the interstices of web material 14c as it migrates therethrough. Thus, only a portion of the fluid stream 12c released from positively-pressured embossing roll 24c will enter negatively-pressured embossing roll 26c while the remainder ensnared within web material 14c enhances the effect of the converting operation performed upon web material 14c (here—matched steel embossing). A manifold provided as vacuum source 46 can be provided with a connection to a pressure control mechanism (not shown). The manifold (e.g., vacuum source 46) ultimately provides an outlet to convey that portion of the fluid stream 12c not entrained within web material 14c away from the processing area.

In an alternative embodiment, the outer surface of the described source plenum in the form of embossing roll 24c is preferably fabricated so that the individual emboss knobs are permeable via openings disposed within the tops of the embossments that ostensibly allow the fluid stream 12c to be fed from an underlying shaped fluid reservoir 44 to the dispersal point of fluid stream 12c from the embossment through channels 42.

Receipt plenum 26c can be fabricated as a negatively-pressured permeable roll having a permeable roll cover disposed upon the surface thereof. In this form, there are no emboss recesses per se. The individual emboss knobs of embossing roll 24c formingly engage the permeable roll cover disposed upon the surface of the negatively-pressured permeable roll providing receipt plenum 26c. When an emboss knobs of embossing roll 24c formingly engages the permeable roll cover disposed upon the surface of the negatively-pressured permeable roll, the permeable roll cover deforms to conform to the geometry of the emboss know contactingly engaged therewith through web material 14c. The permeable roll cover can then allow the fluid stream 12c to be directed toward an underlying source of negative pressure (vacuum source 46) for collection of the remainder of fluid stream 12c (i.e., rogue fluid 32c) from the embossment through channels 42. The degree of coupling between the negatively-pressured permeable roll and the permeable roll cover disposed thereon can be controlled to provide for the desired amount of coupling required to capture rogue fluid 32c emanating from web material 14c.

Figure 7:
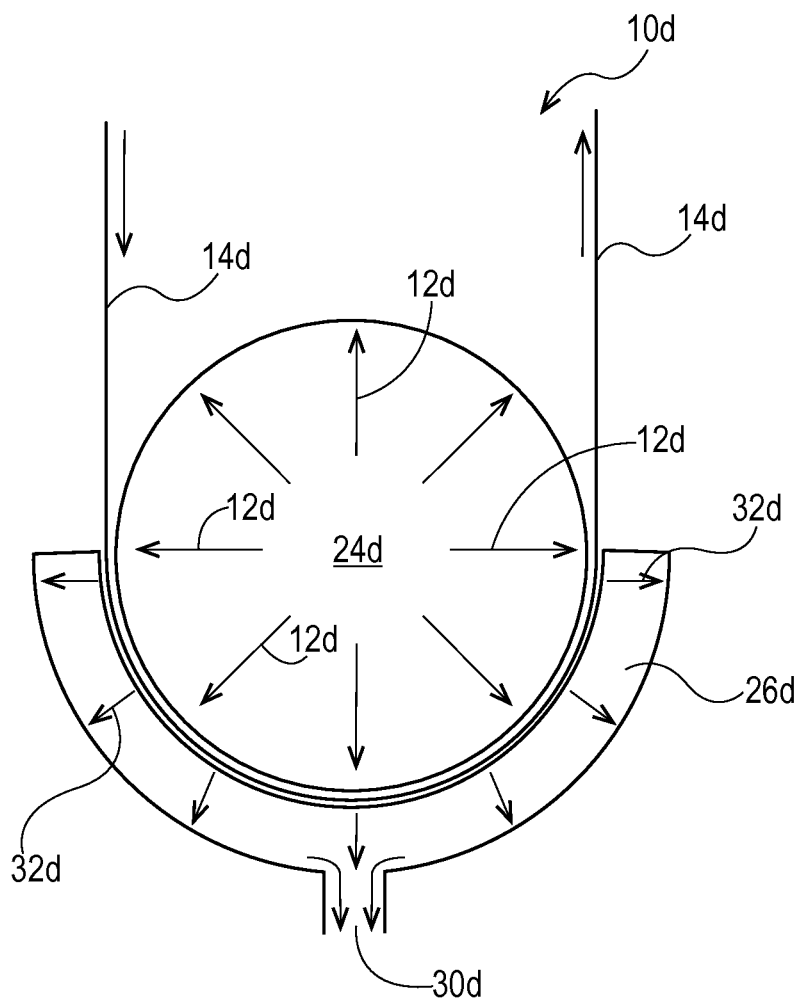
FIG. 7 is a cross-sectional view of yet another alternative embodiment of an apparatus for the application of an atomized fluid to a web substrate.

As shown in FIG. 7, an alternative embodiment of the present disclosure provides for an apparatus 10a for the application of a fluid stream 12d (e.g., steam, lotion, softeners, etc.) to a web material 14d suitable for use with a downstream web material converting process such as an embossing apparatus (not shown). The apparatus 10d generally includes a source plenum in the form of a positively-pressured permeable roll 24d having fluid stream 12d residing therein and an elongate receipt plenum 26d disposed adjacent thereto. In other words, a web material 14d traverses the elongate region formed between a positively-pressured permeable roll 24d having fluid stream 12d residing therein (or otherwise provided internally thereto) and a negatively-pressured elongate receipt plenum 26d so that a fluid originating within positively-pressured permeable roll 24d migrates from the source positively-pressured permeable roll 24d through web material 14d and into re negatively-pressured elongate receipt plenum 26d. In other words, all that is necessary for apparatus 10*d* to function sufficiently is the presence of a pressure gradient between the source plenum and receipt plenum provided.

Again, without desiring to be bound by theory, it is believed that a fluid stream 12*d* released from positively-pressured permeable roll 24*d* can directly impinge upon the surface of web material 14*d* as it traverses the elongate region formed between positively-pressured permeable roll 24*d* and negatively-pressured elongate receipt plenum 26*d*. Such an application would provide increased residence time of the web material 14*d* in the region disposed between positively-pressured permeable roll 24*d* and negatively-pressured elongate receipt plenum 26*d* so that a fluid originating within positively-pressured permeable roll 24*d* will have increased residence time either proximate to web material 14*d* or within web material 14*d*. Such an application can provide enhanced processing capability in any downstream operations intended to further process web material 14*d*. Such an application can also provide enhanced processing speeds due to the presence of negatively-pressured elongate receipt plenum 26*d* since web material 14*d* has a longer residence time within the elongate region formed between positively-pressured permeable roll 24*d* and negatively-pressured elongate receipt plenum 26*d*. In other words the fluid has a longer machine-direction distance to impact the web material.

Also, without desiring to be bound by theory, it is also believed that a portion of fluid stream 12*d* released from positively-pressured permeable roll 24*d* will become entrapped within the interstices of web material 14*d* as it migrates therethrough. Thus, only a portion of the fluid stream 12*d* released from positively-pressured permeable roll 24*d* will enter negatively-pressured elongate receipt plenum 26*d* while the remainder ensnared within web material 14*d* enhances the effect of any downstream converting operations performed upon web material 14*d* such as rubber-to-steel embossing, matched steel embossing, deep nested embossing, compaction, softening, micro-contraction, and combinations thereof.

Positively-pressured permeable roll 24*d* may be driven by means known in the art such that its surface speed substantially matches the speed of the web material 14*d*. Fluid stream 12*d* may be supplied to the interior of positively-pressured permeable roll 24*d* by piping and rotary unions known in the art. The pressure of fluid stream 12*d* may be controlled to a desired target in positively-pressured permeable roll 24*d*. The apertures on the surface of positively-pressured permeable roll 24*d* may be formed by drilling holes of a desired size and the holes may be located in desired locations on the circumferential surface of positively-pressured permeable roll 24*d*. The number of holes drilled and the location of the holes may be selected to create a desired pattern.

The pattern of the holes disposed upon positively-pressured permeable roll 24*d* may determine the pattern of fluid stream 12*d* application. This pattern may be selected to correspond to a pattern of features in the web material 14*d*, including but not limited to embossments, regions of indicia, perforations, and the like. The pattern of fluid stream 12*d* application to the web material 14*d* may also be selected to correspond to other product features including embossing, printing, perforations, combinations thereof, and the like. The circumferential and axial positions of positively-pressured permeable roll 24*d* may be controlled by means known in the art such that the pattern of fluid stream 12*a* application is registered to the web material 14*d* features. Alternatively, the surface apertures may be any desired shape and size, including non-circular and irregular shapes, and created using laser machining or other suitable material removal means. It has been found that such patterned means of fluid stream 12*d* application are surprisingly effective in improving product features such as emboss depth and clarity while preserving web material 14*d* flexibility and softness, which may be compromised when applying fluid stream 12*d* to the entirety of web material 14*d*.

Figure 8:
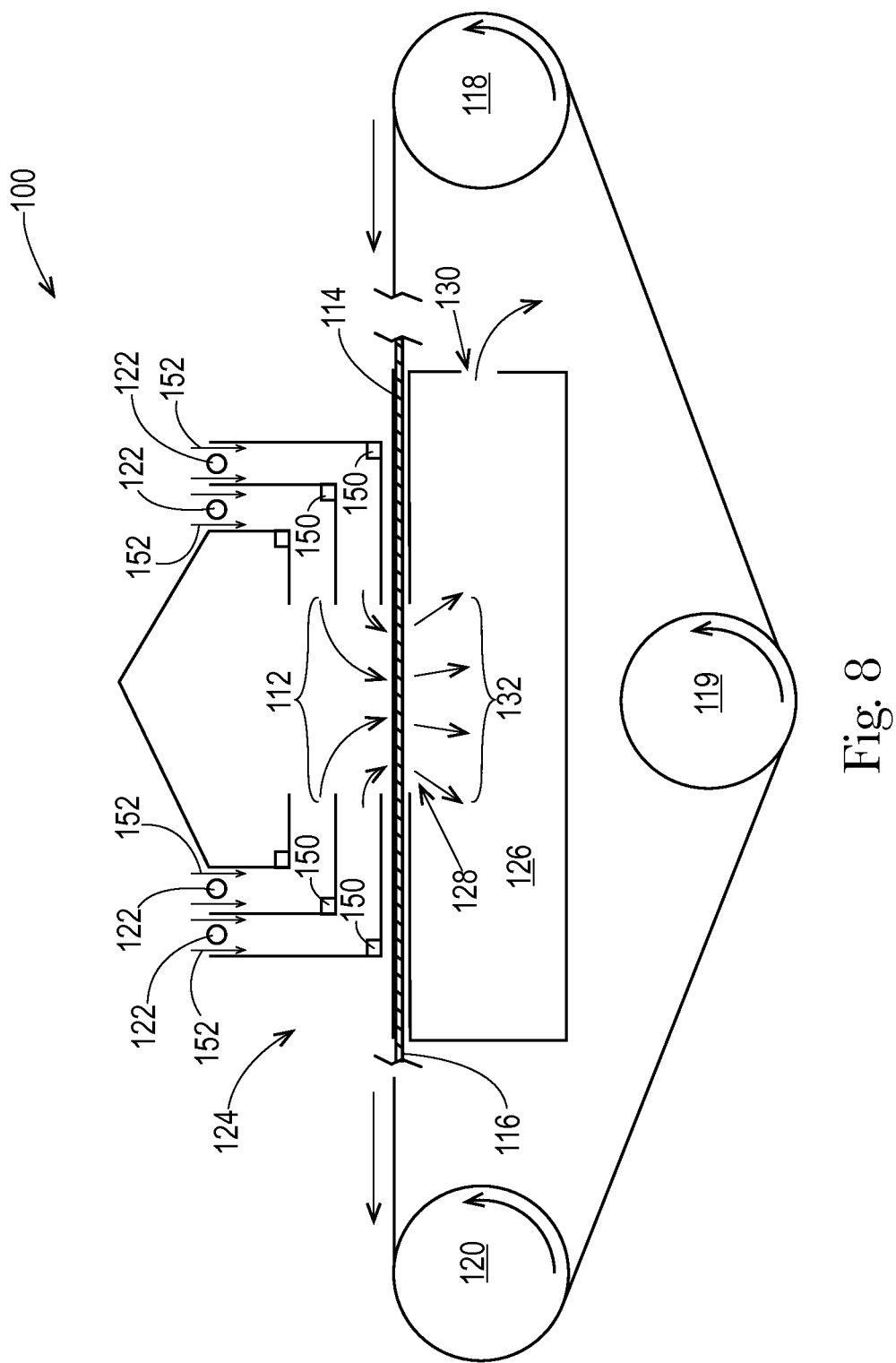
FIG. 8 is a cross-sectional view of yet still another alternative embodiment of an apparatus for the application of an atomized fluid to a web substrate.

As shown in FIG. 8, yet still another alternative embodiment of the present disclosure provides for the application of an atomized fluid stream 112 to a passing web material 114 disposed upon a permeable belt 116. It is believed that the described embodiment can provide any necessary degree of plastic behavior to the web material 114 with the application of the atomized fluid stream 112 that can increase the efficacy of any downstream converting operations, such as embossing. Suitable permeable belts 116 are as described supra.

Prior art attempts to humidify sheet materials may have incorporated the use of humidity chambers. Here, high relative humidity (rh) air can be obtained by injecting steam into air. However, this high relative humidity air remains stagnant in the chamber. Therefore, large residence times to transfer this high relative humidity air are required in order to transfer the high relative humidity air to a moving sheet. Additionally, moisture control and condensation occurring within the chamber are problematic. Further, increased machine speeds require long humidity chambers in order to provide acceptable moisturization of the sheet material. Such long chambers also effectively increase the demand for floor space. Clearly, this form of fluid application to a moving sheet material is deficient.

Returning again to FIG. 8, it became surprisingly apparent that a fluid application process that first nucleates the fluid stream 112 into drops and works like a spray afterwards using a direct spray application was likely a more efficient process. To this end, a unique spray system in the form of apparatus 100 was developed using a fluid source 122 (e.g., consisting of pressure-swirl atomizers) placed in a duct turn 150. In short, a pressure-swirl atomizer having a small orifice diameter can be selected to minimize turbulence and fluid profile and also provide a good distribution of small spray droplets onto the web material 114. A duct turn 150 can eliminate large fluid stream 112 droplets that have a high initial momentum of their own (i.e., have too much initial momentum) and are unable to successfully traverse the duct turn 150 within the pressure stream due to colliding with the duct turn 150. This process results in small droplets exiting the fluid source 122 and duct turn 150 that are provided with additional momentum by a receipt plenum 126 disposed upon on the opposing side of the moving web material 114. The receipt plenum 126 (providing a source of negative pressure, e.g., vacuum, or at least providing a pressure gradient, e.g., having a pressure applied thereto that is sufficiently lower than the pressure provided by fluid source 122) can provide fluid stream 112 flow control and boundary layer air removal from the moving web material 114 at high web material 114 speeds as the web material 114 traverses the region disposed between optional source plenum 124 (e.g., fluid source 122 can be provided internal to source plenum 124 or provided without source plenum 24) and receipt plenum 126. It is believed that the source plenum 124 described infra can provide separation efficiencies of about 50% using vacuum adjustment provided by receipt plenum 126. Additionally, it is believed that the described apparatus 100 can provide fluid stream 112 with smaller droplet sizes with a narrower drop size distribution and at rates sufficient for the addition to a web substrate 114 traversing the region disposed between source plenum 124 and receipt plenum 126. One of skill in the art will recognize that as machine and process speeds increase, the addition rate must also increase.

A suitable source for droplets sizes meeting the need provides fluid source 122 as a pressure swirl atomizer with very small orifice diameter (6-8 mils). The atomizer was capable of reducing the cumulative volume median drop sizes of fluid source 122 to about 30 microns. By using a hooked geometry for droplet impacts in addition to a smaller orifice (such as a Bête Fog atomizer (PJ6)) the cumulative volume median drop sizes of fluid source 122 was reduced to about 22 microns. Incorporating a droplet size separation device into source plenum 124 could reduce the presence of large droplet within fluid stream 112 and also provide a more uniform mass flow rate distribution across the cross machine direction (CD) of the web material 114. Incorporating a droplet size separation device into source plenum 124 was found to reduce the cumulative volume median drop size to about 16 microns.

Without desiring to be bound by theory, it is believed that a correlation exists that can predict fluid stream 112 cumulative volume median drop size as a function of fluid source 112 pressure and orifice size. Using a 6 mil orifice size and a pump pressure was 800 psig one of skill in the art will understand that it may be possible to achieve smaller drop sizes at higher pump pressures according to the following equation:

$$SMD = 2.29\left(\frac{\sigma\mu^2}{\rho_a}\right)^{0.25} P^{-0.5} t^{0.25} + 0.89\left(\frac{\sigma\rho_L}{\rho_a}\right)^{0.25} P^{-0.25} t^{0.75},$$

where:
σ=the surface tension coefficient;
μ=the liquid viscosity;
$\rho_a$=the density of air;
$\rho_L$=the density of the liquid;
P=the atomizer pressure; and,
t=the liquid film thickness.

The film thickness through the fluid source 112 can be expressed by the following equation:

$$t = 3.66\left(\frac{d_0 m_L \mu}{\rho_L P}\right)^{0.25},$$

where:
$d_0$=the orifice diameter; and,
$m_L$=the liquid flow rate.
The SMD can be defined as $$\frac{\sum N_i D_i^3}{\sum N_i^2 D_i^2}.$$

This relationship provides a diameter that is a weighted average of the volume to surface ratio of the spray. The Sauter mean diameter (SMD) can be converted to cumulative volume median diameter ($d_{v0.5}$) at which, 50% by volume of the drops from fluid source 112 have smaller diameter. Further, if drop velocities are 2000 fpm vertical to the web material 114 surface at about a distance of 6 inches from the web material 114, the fluid stream 112 droplets having a size ranging from 10-100 microns are not able to reach the web material 114 surface because of the boundary layer air flow carrying them away for a 2000 fpm web material 114 speed.

Returning again to FIG. 8, a receipt plenum 126 and a permeable belt 116 can be provided to control the web material 114 humidity addition rate from the source plenum 124 and support the web material 114 on the side opposing source plenum 124 and in contacting engagement with permeable belt 116. Without desiring to be bound by theory, it is believed that the receipt plenum 126 provided herein can facilitate the removal of any boundary layer from web material 114 and allow small drops from fluid stream 112 to access the web material 114 at increased line speeds.

As discussed supra, the source plenum is preferably capable of separating the large drops in fluid stream 112 emanating from fluid source 122 and distribute the remaining small drops in the cross machine direction and deposit them more uniformly at a required addition level onto web material 114 as web material 114 traverses the region disposed between source plenum 124 and receipt plenum 126.

Source plenum is preferably provided with a plurality of fluid sources 122 disposed within the source plenum 124. The source plenum 124 is also preferably provided with ductwork comprising flow turn or turns 150. Again without desiring to be bound by theory, it is believed that larger drops (>36 microns) emanating from fluid source 122 will have high initial (i.e., too much initial) momentum to traverse the path to final impingement upon web material 114 and terminate their progression on a wall disposed inside source plenum 124 proximate to one of flow turn or turns 150. These large droplets are hypothesized to form liquid film flows on wall surfaces and can be removed by appropriate ducting provided by one of skill in the art. The remaining droplets from fluid source 122 can spread in the CD direction and leave the source plenum 124 relatively uniformly. Fluid source 122 is preferably formed using a pressure atomizer model PJ6 from Bête Fog Company. However, one of skill in the art would realize that any atomizer having a similar drop size range will provide acceptable results. It was found the cumulative volume median drop size ($d_{v05}$) from this atomizer was about 22 microns. The median drop size can then be reduced to about 16 microns at the exit of this source plenum 124 using a single flow turn 150. For example, one of skill in the art could also incorporate a Universal Fog atomizer having a 6 mil orifice into fluid source 122.

Additionally, one of skill in the art could provide a butterfly valve proximate to the terminus of any ductwork provided in source plenum 124 as well as flow restricting plates at the inlet to any ductwork within source plenum 124 provide additional control of airflow 152 and fluid source 122 droplet flow rates. Such a valve and flow restricting plate arrangement could also be used by one of skill in the art to further reduce the fluid source 122 droplet size.

Exemplary embodiments of several fluid sources 122 suitable for use with source plenum 124 are discussed infra. As presented, two atomizers were used and spaced 5.5" apart.

Case 1: For air assist atomization, Spraying Systems atomizers (model # SU13A) were used to create flat sprays. The atomizers were aligned along their longer axis to provide the maximum coverage. The air pressure was set at 40 psig and the total water flow rate to both atomizers was 38 grams/min.

Case 2: For pressure atomization, Universal Fog atomizers of 6 mil orifice diameter were used to create round sprays. The supply water pressure was 800 psig and the water flow rate was about 65 grams/min for each atomizer.

Case 3: Spray duct or separator was used together with the 6 mil Universal Fog atomizers. The spray induced air flow by entraining surrounding air which carried the small drops to the duct exit. The large drops were separated and formed liquid films on duct walls and were drained. The velocity of the low speed drops were measured at 0.75" from the exit of the duct half way between the front and back walls.

The droplets from fluid source 122 generally leave the source plenum 124 with low velocity. It is believed that most of the momentum of the droplets is transferred to the duct and the induced air flow from make-up air 152 provides any necessary momentum to carry the small droplets. The source plenum 124 was observed to spread the drops across the CD and can provide a relatively uniform drop velocity profile. The rms velocities can also be very low, but compared to the magnitude of the mean velocity, they have the same order of magnitude. One of skill in the art will recognize that the apparatus 100 can provide uniform drop sizes and uniform resulting web material 114 moistures. However, the apparatus 100 can be configured to provide any drop size distribution and web material 114 moisture profile desired. It is believed that virtually any scenario can be provided with an appropriate configuration of turn 150 which can provide a large droop separation and/or air flow/drop spreading effect in the CD of web material 114.

The present apparatus 100 was found to perform best with the use of receipt plenum 126 providing a source of negative pressure upon the opposing side of the web material 114. The receipt plenum 126 can provide the necessary directivity to the resulting droplets emanating from source plenum 124 and can also increase their momentum and mass flow rate. This can be important for the very low flow velocities typically suitable for source plenum 124 in conjunction with the web materials 114 described supra. The use of receipt plenum 126 was found to increase the very low spray drop velocities and ergo, increase the moisture addition rate to the web material 114.

Further, the coefficient of variation for web material 114 moisture formed by apparatus 10 was found to be less than about 20% in the CD and about 10% in the MD. At any rate, the bulk of the flow control of droplets emanating from fluid source 122 and impinging upon web material 114 was found to be proportional to the vacuum level adjustment. This performance can be changed by changing the amount of negative pressure present within receipt plenum 126 by adjusting a vacuum fan speed positioned near exhaust 130. For example, the approach velocity of a droplet emanating from source plenum 124 relative to web material 114 can be determined by measuring the air flow rate at the make-up air 152 inlet to source plenum 124 and dividing by the entrance area through which the air was pulled into the receipt plenum 126. A preferred approach velocity can be about 1300 fpm.

In operation, the present invention captures at least a portion of the vapor component without substantial dilution and without condensation of the vapor component in the drying system. The collection of the vapor component at high concentrations permits efficient recovery of the material. The absence of condensation in the drying system reduces product quality issues involved with condensate falling onto the product. The present invention also utilizes relatively low air flow which significantly reduces the introduction of extraneous material into the drying system and thus prevents product quality problems with the finished product.

All publications, patent applications, and issued patents mentioned herein are hereby incorporated in their entirety by reference. Citation of any reference is not an admission regarding any determination as to its availability as prior art to the claimed invention.

The dimensions and/or values disclosed herein are not to be understood as being strictly limited to the exact numerical values recited. Instead, unless otherwise specified, each such dimension and/or value is intended to mean both the recited dimension and/or value and a functionally equivalent range surrounding that dimension and/or value. For example, a dimension disclosed as "40 mm" is intended to mean "about 40 mm".

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for the application of atomized fluid to a permeable web material having a first surface, a second surface opposed thereto, a machine direction, and a cross-machine direction orthogonal and co-planar thereto, the apparatus comprising:
    a fluid source disposed in proximate fluid contact with said first surface of said web material, said fluid source comprising a positively pressured permeable roll, said positively pressured permeable roll having apertures disposed therein, said apertures providing fluid communication between an inner portion of said positively pressured permeable roll and a surface thereof, said positively pressured permeable roll having said atomized fluid disposed therein, said atomized fluid being disposable from said inner portion to said surface through said apertures and into contacting engagement with said permeable web material when said permeable web material is at least proximate to said surface;
    a receipt plenum having at least one opening disposed adjacent said second surface of said web material, said receipt plenum providing a source of negative pressure to said second surface of said web material through a portion of said at least one opening;
    wherein said atomized fluid disposed from said fluid source contacts said first surface of said permeable web material and is caused to traverse therethrough by said source of negative pressure; and,
    wherein a portion of said atomized fluid contacting said first surface of said web material is contained by said receipt plenum.

2. The apparatus of claim 1 wherein said receipt plenum comprises a negatively-pressured permeable roll having at least one aperture disposed therein, said at least one aperture providing fluid communication between an inner portion of said negatively-pressured permeable roll and a surface thereof.

3. The apparatus of claim 2 wherein said atomized fluid is disposable from said surface of said negatively-pressured permeable roll to an inner portion thereof through said at least one aperture when said permeable web material is at least proximate to said surface of said negatively-pressured permeable roll.

4. The apparatus of claim 3 wherein said atomized fluid is disposable from said surface of said negatively-pressured permeable roll to an inner portion thereof through said at least one aperture only when said permeable web material is in contacting engagement with said surface of said negatively-pressured permeable roll.

5. The apparatus of claim 2 wherein said surface of said positively pressured permeable roll further comprises embossing elements disposed thereon, said embossing elements cooperatively engaging said surface of said negatively pressured permeable roll.

6. The apparatus of claim 5 wherein said surface of said negatively pressured permeable roll further comprises embossing elements disposed thereon, said elements disposed upon said surface of said positively pressured permeable roll cooperatively engaging said elements disposed upon said surface of said positively pressured permeable roll.

7. The apparatus of claim 5 wherein a portion of said at least one aperture cooperatively engages said embossing elements disposed upon said surface of said positively pressured permeable roll.

8. The apparatus of claim 1 wherein said atomized fluid is disposable from said inner portion to said surface through a portion of said at least one aperture and into contacting engagement with said permeable web material only when said permeable web material is in contacting engagement with said surface.

9. The apparatus of claim 1 wherein said apparatus provides substantially uniform flow of said atomized fluid through said web material when said web material is disposed proximate to both said positively-pressured permeable roll and said source of negative pressure.

10. The apparatus of claim 9 wherein said positively-pressured permeable roll and said source of negative pressure are disposed to minimize any make-up air being drawn through said web material and into said source of negative pressure.

11. The apparatus of claim 1 wherein said receipt plenum is disposed about a portion of the surface of said positively-pressured permeable roll, said receipt plenum providing a source of negative pressure to said second surface of said web material.

12. The apparatus of claim 1 wherein said receipt plenum provides a negative pressure adapted to provide said atomized fluid traversing through said permeable web material with a residence time within said permeable web.

13. The apparatus of claim 12 wherein said receipt plenum provides said negative pressure to said permeable web material while said permeable web material traverses said at least one aperture.

14. The apparatus of claim 1 wherein said fluid source provides said atomized fluid to at least one discrete portion of said permeable web material, said at least one discrete portion being disposed in said cross-machine direction of said permeable web material and in registration with a downstream process.

15. The apparatus of claim 14 wherein said fluid source provides said atomized fluid to a plurality of said least one discrete portions, said plurality of said least one discrete portions forming a pattern upon said permeable web material.

16. The apparatus of claim 1 wherein said fluid source and said receipt plenum form a pressure gradient therebetween.

17. The apparatus of claim 1 wherein said apparatus has a mass flow rate, said mass flow rate within said apparatus being approximately equal to an emission rate of said atomized fluid from said fluid source.

18. The apparatus of claim 1 wherein said fluid is selected from the group consisting of opacifying agents, optical enhancing agents, optical brighteners, surface energy modifiers, inks, dyes, softening agents, cleaning agents, dermatological solutions, wetness indicators, adhesives, botanical compounds, skin benefit agents, medicinal agents, lotions, fabric care agents, dishwashing agents, carpet care agents, surface care agents, hair care agents, air care agents, water, steam, actives comprising a surfactant selected from the group consisting of: anionic surfactants, cationic surfactants, nonionic surfactants, zwitterionic surfactants, and amphoteric surfactants, antioxidants, UV agents, dispersants, water, steam, disintegrants, antimicrobial agents, antibacterial agents, oxidizing agents, reducing agents, handling/release agents, perfume agents, perfumes, scents, oils, waxes, emulsifiers, dissolvable films, edible dissolvable films containing drugs, pharmaceuticals and/or flavorants, and drugs selected from the group consisting of: analgesics, anti-inflammatory agents, anthelmintics, antiarrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, blood products and substitutes, cardiac inotropic agents, corticosteroids, cough suppressants, diagnostic agents, diuretics, dopaminergics, haemostatics, immunological agents, lipid regulating agents, muscle relaxants, parasympathomimetics, parathyroid calcitonin and biphosphonates, prostaglandins, radiopharmaceuticals, sex hormones, steroids, anti-allergic agents, stimulants and anorexics, synpathomimetics, thyroid agents, PDE IV inhibitors, NK3 inhibitors, CSBP/RK/p38 inhibitors, antipsychotics, vasodilators, xanthenes, and combinations thereof.

19. The apparatus of claim 1 wherein said atomized fluid experiences a phase change while traversing though said permeable web material.

20. The apparatus of claim 1 wherein a portion of said at least one aperture is disposed upon said surface of said positively pressured permeable roll in a pattern.

* * * * *